(12) United States Patent
Cooper

(10) Patent No.: US 7,511,281 B2
(45) Date of Patent: Mar. 31, 2009

(54) ULTRAVIOLET LIGHT TREATMENT CHAMBER

(75) Inventor: James Randall Cooper, San Diego, CA (US)

(73) Assignee: Ultraviolet Sciences, Inc., San Diego, CA (US)

( * ) Notice: Subject to any disclaimer, the term of this patent is extended or adjusted under 35 U.S.C. 154(b) by 603 days.

(21) Appl. No.: 11/217,772

(22) Filed: Aug. 31, 2005

(65) Prior Publication Data

US 2007/0045561 A1 Mar. 1, 2007

(51) Int. Cl.
*G01N 23/00* (2006.01)
*H01J 37/20* (2006.01)

(52) U.S. Cl. .............. 250/432 R; 250/453.11; 250/454.11; 250/492.1; 250/493.1; 250/455.11; 210/199; 422/24; 422/186.3; 422/121; 422/186.04; 118/642; 427/595

(58) Field of Classification Search ............ 250/455.11, 250/453.11, 454.11, 492.1, 493.1, 432 R; 210/199; 422/24, 186.3, 121, 186.04; 118/642; 427/595
See application file for complete search history.

(56) References Cited

U.S. PATENT DOCUMENTS

| | | | |
|---|---|---|---|
| 2,072,416 A | 3/1937 | Berndt et al. |
| 2,072,417 A | 3/1937 | Berndt et al. |
| 2,482,507 A | 9/1949 | Rentschler et al. |
| 3,569,754 A | 3/1971 | Priebe et al. |
| 3,572,391 A | 3/1971 | Hirsch |
| 3,814,680 A | 6/1974 | Wood |
| 3,941,670 A | 3/1976 | Pratt |
| 4,008,045 A | 2/1977 | Free |
| 4,042,325 A | 8/1977 | Tensmeyer |
| 4,042,850 A | 8/1977 | Ury et al. |
| 4,112,335 A | 9/1978 | Gonser |
| 4,141,686 A | 2/1979 | Lewis |
| 4,207,541 A | 6/1980 | Karger et al. |
| 4,232,276 A | 11/1980 | Iwata |
| 4,304,996 A | 12/1981 | Blades |
| 4,327,276 A | 4/1982 | Injushin et al. |
| 4,336,223 A | 6/1982 | Hillman |
| 4,400,270 A | 8/1983 | Hillman |
| 4,469,835 A | 9/1984 | Laurin |
| 4,507,587 A | 3/1985 | Wood et al. |
| 4,534,282 A | 8/1985 | Marinoza |

(Continued)

FOREIGN PATENT DOCUMENTS

EP 0277505 8/1988

OTHER PUBLICATIONS

PCT International Search Report and Written Opinion of the International Searching Authority from PCTUS0631643 dated Jan. 16, 2008.

(Continued)

*Primary Examiner*—Jack I Berman
*Assistant Examiner*—Meenakshi S Sahu
(74) *Attorney, Agent, or Firm*—Fitch, Even, Tabin & Flannery

(57) ABSTRACT

This invention relates generally to methods and apparatuses for the treatment of liquids and gases using ultraviolet light. In one embodiment, a substantially enclosed chamber coated with a reflective material containing an ultraviolet lamp and an ultraviolet transmissive tube running through the chamber for the treatment of liquid passed therethrough is disclosed.

22 Claims, 4 Drawing Sheets

Chamber sketch

U.S. PATENT DOCUMENTS

| | | |
|---|---|---|
| 4,535,247 A | 8/1985 | Kurtz |
| 4,601,822 A | 7/1986 | Zamburro |
| 4,643,464 A | 2/1987 | Weinhold |
| 4,766,321 A | 8/1988 | Lew et al. |
| 4,769,131 A | 9/1988 | Noll et al. |
| 4,786,812 A | 11/1988 | Humphreys |
| 4,831,268 A | 5/1989 | Fisch et al. |
| 4,866,282 A | 9/1989 | Miripol et al. |
| 4,871,559 A | 10/1989 | Dunn et al. |
| 4,887,008 A | 12/1989 | Wood |
| 4,887,192 A | 12/1989 | Simpson et al. |
| 4,902,411 A | 2/1990 | Lin |
| 4,919,951 A | 4/1990 | Jensen et al. |
| 4,948,980 A | 8/1990 | Wedekamp |
| 4,971,687 A | 11/1990 | Anderson |
| 5,023,460 A | 6/1991 | Foster, Jr. et al. |
| 5,037,618 A | 8/1991 | Hager |
| 5,048,404 A | 9/1991 | Bushnell et al. |
| 5,120,450 A | 6/1992 | Stanley, Jr. |
| 5,151,252 A | 9/1992 | Mass |
| 5,208,461 A | 5/1993 | Tipton |
| 5,227,637 A | 7/1993 | Herold et al. |
| 5,230,792 A | 7/1993 | Sauska et al. |
| 5,247,178 A | 9/1993 | Ury et al. |
| 5,288,647 A | 2/1994 | Zimlich, Jr. et al. |
| 5,302,356 A | 4/1994 | Shadman et al. |
| 5,395,591 A | 3/1995 | Zimlich, Jr. et al. |
| 5,446,289 A | 8/1995 | Shodeen et al. |
| 5,451,367 A | 9/1995 | Stark et al. |
| 5,498,394 A | 3/1996 | Matschke |
| 5,597,482 A | 1/1997 | Melyon |
| 5,626,768 A | 5/1997 | Ressler et al. |
| 5,686,789 A | 11/1997 | Schoenbach |
| 5,768,853 A | 6/1998 | Bushnell |
| 5,814,523 A | 9/1998 | Zimlich, Jr. et al. |
| 5,843,309 A | 12/1998 | Mancil |
| 5,916,439 A | 6/1999 | Oleskow |
| 5,925,885 A | 7/1999 | Clark et al. |
| 5,939,829 A | 8/1999 | Schoenbach |
| 6,013,918 A | 1/2000 | Bushnell |
| 6,027,754 A | 2/2000 | Bushnell et al. |
| 6,030,578 A | 2/2000 | McDonald |
| 6,054,097 A | 4/2000 | Mass et al. |
| 6,072,273 A | 6/2000 | Schoenbach |
| 6,083,387 A * | 7/2000 | LeBlanc et al. ............. 210/199 |
| 6,150,663 A | 11/2000 | Rosenthal |
| 6,190,609 B1 | 2/2001 | Chapman et al. |
| 6,228,332 B1 | 5/2001 | Dunn et al. |
| 6,346,770 B1 | 2/2002 | Schoenbach |
| 6,433,344 B1 | 8/2002 | Salisbury et al. |
| 6,589,489 B2 * | 7/2003 | Morrow et al. ........... 422/186.3 |
| 2003/0060747 A1 | 3/2003 | Fries et al. |
| 2004/0144733 A1 | 7/2004 | Cooper |
| 2004/0166018 A1 | 8/2004 | Clark |
| 2005/0115498 A1 * | 6/2005 | Ingram et al. ................ 118/642 |

OTHER PUBLICATIONS

Aquafine Wedeco Environmental Systems Inc. "Water Disinfection with Ultraviolet Light" 1996, 22 pp.

Bender, "Photolytic oxidation of contaminated water using a high-energy, pulsed ultra-violet flashlamp operating in the blackbody regime." OSA Symposium. 1997, pp. 1-14.

Dunn, "PureBright: Sterilization Using Intense Pulsed Light" Summary of Presentation to International Society of Pharmaceutical Engineers Dec. 1995, 11 pp.

Jagger, "Introduction to Research in Ultraviolet Photo Biology" 1967, pp. 1-164.

Rentschler, et al. "Bactericidal Effect of Ultraviolet Radiation" Research Department, Westinghouse Lamp Division. Bloomfield, New Jersey. pp. 745-774.

Zimmerman, et al "Electrical Breakdown, Electropermeabilization and Electrofusion" *Physiology Biochemistry Pharmacology*. vol. 105 1986, pp. 176-256.

Bolten, J.R., Ultraviolet Applications Handbook, 2nd Edition 2001, Photosciences Inc., p. 37.

Cooper, U.S. Appl. No. 11/959,445.

\* cited by examiner

Figure 1. Chamber sketch

ULTRAVIOLET LIGHT TREATMENT CHAMBER

BACKGROUND OF THE INVENTION

1. Field of the Invention

This invention relates generally to methods and apparatuses for the treatment of liquids and gases using ultraviolet light.

2. Discussion of the Related Art

There is a particular need for methods and apparatuses useful for sterilizing and/or reducing contamination in liquids and gases, such as in municipal drinking water supplies, ultrapure water systems for industrial processing and pharmaceutical manufacture, water and reagents for use in experimentation, gases used in sterile rooms, and the like. Such methods and apparatuses may be advantageously used to reduce or eliminate the need for chemical aerosols, chemical preservatives, microfiltration, and like materials and processes for the sterilization of liquids and/or gases.

Apparatus for irradiating media by means of a UV light external to a tubular body has been described, such as in U.S. Pat. No. 4,948,980, which is incorporated herein by reference. U.S. Pat. No. 4,948,980 provides an apparatus consisting of a tubular body through which medium to be irradiated flows, and at least two UV light sources with reflectors arranged externally to the tubular body and having parallel axes. The apparatus described in U.S. Pat. No. 4,948,980 relies on specular reflectors to control the uniformity of the light pattern delivered by the lamps. The lamp sources are relatively flat and aligned on their edges within the specular reflector in order to minimize the optical effects in the reflector. U.S. Pat. No. 4,948,980 does not appreciate the use of a high reflectivity diffuse reflector to treat a liquid or gas with a low absorption cross section, nor, does the patent anticipate a large increase in dose delivered to a target as the net reflectivity of the entire chamber approaches 100 percent.

United States Patent Publication No. 2004/0166018, herein incorporated by reference, describes a UV air sterilization chamber comprising inner surfaces having a diffuse reflective behavior. The sterilization chamber includes an inlet aperture and an outlet aperture for air to flow through the chamber and a light source emitting a UV light. US Patent Publication No. 2004/0166018 does not attempt to increase the transparent or translucent containment volume compared to total chamber volume to maximize performance of the apparatus.

In U.S. Pat. No. 6,228,332, herein incorporated by reference, short-duration, high-intensity pulsed broad-spectrum polychromatic light is used to treat water for the deactivation of microorganisms. As described in U.S. Pat. No. 6,228,332, deactivation of microorganisms in water involves illuminating the water with at least one short-duration, high-intensity pulse of broad-spectrum polychromatic light. The system includes a watertight housing having an inlet port and an outlet port for the flow water. A tubular light source for deactivating microorganisms and a tubular baffle for directing the water flow are positioned within the watertight housing. Water enters the inlet port and flows between the watertight housing and the tubular baffle in one direction, around the end of the tubular baffle and back through the center of the tubular baffle in a second direction exiting the outlet port. In this case, water flows around the tubular light source which provides at least one short-duration, high-intensity pulse of broad-spectrum polychromatic light. However, not described in U.S. Pat. No. 6,228,332 is the use of a reflective surface and substantially enclosing the treatment chamber for achieving maximum efficiency in the treatment of a liquid or gas target.

The present invention addresses the above and other needs.

SUMMARY OF THE INVENTION

The present invention relates generally to methods and apparatuses for the treatment of liquids and gases using ultraviolet light.

In one embodiment, an apparatus for the treatment of a liquid or gas is described. The apparatus comprises a chamber which is at least 80 percent enclosed, an ultraviolet lamp contained within the chamber, an ultraviolet transmissive tube running through the chamber for the passage of a liquid or gas therethrough, and a reflective material coating or limiting the inside of the chamber, wherein the material is at least 80 percent reflective.

In one embodiment, the ultraviolet irradiance impinging on the liquid or gas is in the range of about 0.01 W/cm$^2$ and 20 W/cm$^2$.

In one embodiment, the reflective material may be a reflector such as a diffuse reflector or a specular reflector, which may extend to a distance beyond the active portion of the ultraviolet lamp. The reflector material may be any of polyfetrafluoroethylene (PTFE), expanded polytetrafluoroethylene (ePTFE), or other similar plastics; or coated, anodized, or polished aluminum.

In another embodiment the reflective material is a coating on the inside of the chamber, wherein the reflective coating may be a mixture of binder and one or more reflecting additives such as barium sulfate, magnesium fluoride, magnesium oxide, aluminum oxide, titanium oxide, holmium oxide, calcium oxide, lanthanum oxide, germanium oxide, tellurium oxide, europium oxide, erbium oxide, neodymium oxide, samarium oxide, ytterbium oxide, zirconium oxide, or any other oxides, or other reflective material which can be deposited as a coating to produce a high reflectivity surface.

In another embodiment, the chamber may include baffles. In yet another embodiment, the chamber may have an input and/or output port for the ultraviolet transmissive tube to enter and/or exit the chamber. The input and/or output ports may be configured in a serpentine path.

BRIEF DESCRIPTION OF THE DRAWINGS

The above mentioned and other objects and features of the present embodiment and the manner of attaining them will become apparent, and the present embodiments themselves will be best understood by reference to the following description in conjunction with the accompanying drawings, wherein.

DETAILED DESCRIPTION OF THE PREFERRED EMBODIMENTS

Figure 1:
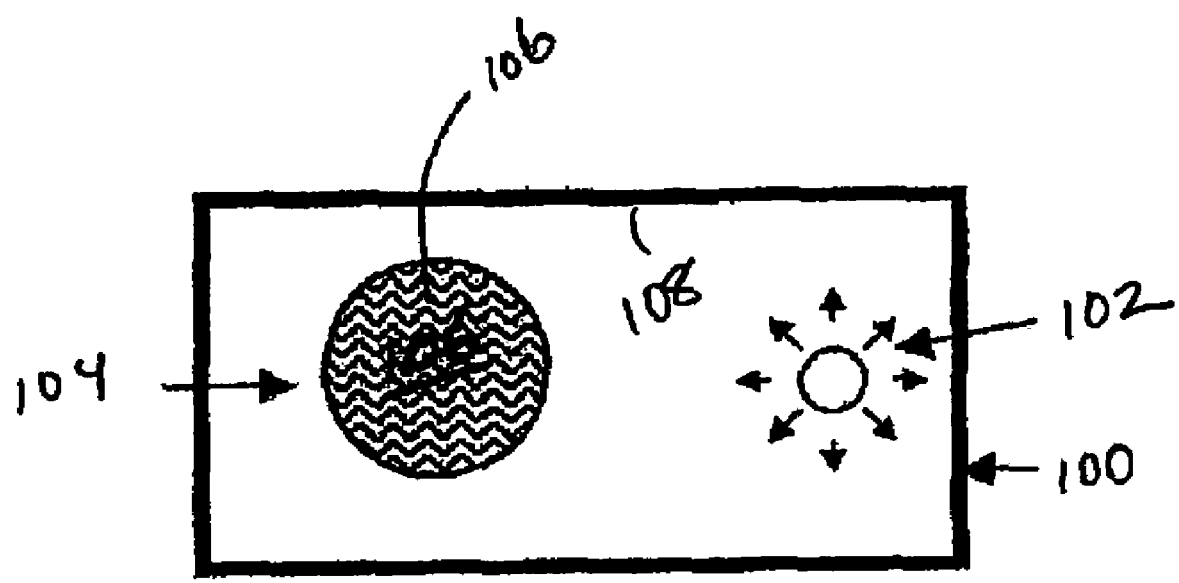
FIG. 1 is schematic showing an overview of the preferred embodiment.

The following is a description including the best mode presently contemplated for practicing the invention. This description is not to be taken in a limiting sense, but is made merely for the purpose of describing the general principles of the invention. The scope of the invention should be ascertained with reference to the issued claims.

The apparatus described herein provides for a large reduction in the total UV power required to treat a target liquid or gas to a specified dose level. This is accomplished by enclosing the target and the UV light source within a chamber which has walls with an extremely high reflectivity lining or coating and by minimizing the size and number of openings in the chamber wall and absorbing surfaces within the chamber. The chamber design allows for increased photon deposition resulting in enhanced UV irradiation efficiency. Synergy is achieved by combining both of these criteria because the dose delivered to the target increases exponentially as the chamber wall reflectivity and the percentage of the chamber enclosed approach 100 percent. The resulting synergistic effect is more efficient than the singular effect of each of the criteria in sum. For example, a fully enclosed chamber with 99% reflective walls will deliver 10 times the dose to the target that an identical chamber with 90% reflective walls will.

Treatment of a liquid or gas within a transmissive tube to separate the liquid or gas from the chamber walls has advantages. Such a tube could be introduced into the chamber described above. In order to maximize the dose delivered to the target within the transmissive tube and transmissive media carrying the target inside the tube, the transmissive tube should enclose as much of the chamber volume as possible. This minimizes the amount of light which is reflected between walls without passing through the transmissive tube and into the target area.

Ultraviolet light, which has shorter wavelengths than visible light, is considered to include wavelengths measuring between 10 and 400 nm, generally corresponding to frequencies between $7.5 \times 10^{14}$ to $3 \times 10^{16}$ Hz. On the electromagnetic spectrum, ultraviolet light has wavelengths less than violet light in the visible spectrum and wavelengths greater than X rays. Ultraviolet light is divided into three categories, near ultraviolet (NUV), which is closest to visible light and consists of wavelengths from 400 to 100 nm; far ultraviolet (FUV), located after NUV and consists of wavelengths from 300 to 200 nm; and extreme ultraviolet (EUV) which is located after FUV and before X ray and consists of wavelengths from 200 to 100 nm. Ultraviolet light is also divided, based on biological effects, into UV-A (400 to 315 nm), UV-B (318 to 280 nm), and UV-C (280 to 100 nm) bands which do not directly correspond to the aforementioned designations.

While most UV irradiation processes can occur when stimulated by UV photons with wavelengths longer than 200 nm, many applications use sub-200 nm light to increase the process rates. In this regime, the efficiency of most light sources is relatively low. This low efficiency further drives the need for an efficient system to deliver the UV photons to their desired target.

Generally, methods and apparatuses for the treatment of liquids and gases using ultraviolet light are described herein below. Although the following description is particularly directed to the treatment of liquid and gaseous materials, it should be understood that the apparatus of the present embodiment may be easily adapted for the treatment of solid materials, such as particles in suspension or emulsions, foodstuffs, surgical instruments, and the like. For example, the treatment chamber may be adapted to remove the tubing material and input and output ports and replaced with a cavity for the placement of a solid material. This arrangement may render the treatment chamber fully or nearly fully enclosed. Besides solid materials, liquids and gases enclosed in a container, such as vials of reagents, pouches of blood and blood components, and other prepackaged liquids and gases may be treated using a slightly modified apparatus.

Ultraviolet light is useful for deactivating or killing microorganisms including bacteria, viruses, fungi, mold spores, protozoa, and the like biological materials. Deactivation is caused when ultraviolet radiation alters or mutates biomolecules such nucleic acids, i.e. deoxyribonucleic acid (DNA) and/or ribonucleic acid (RNA) and proteins, e.g. enzymes. When native DNA is exposed to a sufficient level of ultraviolet radiation, mutations are formed in the genetic material. The most common mutations are the 5,6-cyclbutyl dipyrimidines, pyrimidine dimers, pyrimidine adducts, pyrimidine hydrates, and DNA-protein crosslinks. Direct protein damage is less common but indirect damage of other biomolecules via proteins absorbing wavelengths greater than 290 nm is particularly relevant; proteins absorbent at these wavelengths generally contain tryptophan and tyrosine. In the presence of oxygen, energy transfer from the excited triplet state of tryptophan to oxygen occurs producing a singlet oxygen. Thus, tryptophan in protein acts as an endogenous photosensitizer in the UVB wavelength range by producing free radical oxygen, which reacts with proteins, unsaturated lipids, and bases in nucleic acids. In any case ultraviolet radiation promotes the generation of singlet oxygen and hydroxyl free radicals which can cause damage to cellular proteins, lipids, and carbohydrates.

Membraneous microorganisms are deactivated or killed when ultraviolet radiation penetrates the organism's membrane and alters its genetic material and, to a lesser extent, proteins (e.g. enzymes). In cases where an organism has sustained significant biomolecular damage, the microorganism may die. In cases where the genetic and/or proteinaceous material has been altered, but perhaps not completely destroyed, the microorganism may no longer be able to reproduce. Without the ability to reproduce, coupled with the short lifespan of most microorganisms, population size will diminish rapidly in material treated with ultraviolet radiation.

In the case of viruses, ultraviolet radiation mutates the genetic material such that the virus is no longer capable of infecting host cells and/or multiplying within a host organism using the host's cellular machinery. The UV dose for deactivating typical bacteria such as *Enterobacteria cloacae, Klebsiella pneumoniae, Pseudomonas aeruginosa, Salmonella typhimurium* A, *Vibrio cholerae,* and *Escherischia coli* is between 20 and 30 mJ/cm$^2$. For spore forming bacteria such as *Bacillus subtilis* in the sporulated state, the dose is higher, usually at least 60 mJ/cm$^2$. Deactivation of viruses such as polio and rotavirus requires a dose between 30 and 40 mJ/cm$^2$, but other viruses can require higher doses. Protozoa such as *Cryptosporidium parvum* and *Giardia muris* have been killed with doses as low as 10 mJ/cm$^2$ (*Ultraviolet Applications Handbook,* 2nd ed., James R. Bolton, Bolton Photosciences, Inc., 2001, p. 37).

Ultraviolet light is also used to decompose chemicals, particularly organic chemicals, into components which are safer or which can be more easily removed by activated carbon filtration, resin beds, or reverse osmosis, any of which are features which may be used in conjunction with the apparatus and methods described herein. This decomposition results from both direct photon absorption or by decomposition by OH— radicals which are produced in the proximity of the chemical molecule by the interaction of the ultraviolet light with water molecules or possibly other sources of OH— radicals.

A table of dissociation wavelengths and the maximum wavelength which can cause this dissociation for common chemical bonds in organic substances is shown below.

| Dissociation Energies for Interatomic Bonds in Organic Substances | | |
|---|---|---|
| Chemical Bond | Dissociation Energy (UV Dose) [kcal/gmol] | Maximum Wavelength for Dissociation [nm] |
| C—C | 82.6 | 346.1 |
| C=C | 14.5 | 196.1 |
| C≡C | 199.6 | 143.2 |
| C—Cl | 81.0 | 353.0 |
| C—F | 116.0 | 246.5 |
| C—H | 98.7 | 289.7 |
| C—N | 72.8 | 392.7 |
| C=N | 147.0 | 194.5 |
| C≡N | 212.6 | 134.5 |
| C—O | 85.5 | 334.4 |
| C=O (aldehydes) | 176.0 | 162.4 |
| C=O (ketones) | 179.0 | 159.7 |
| C—S | 65.0 | 439.9 |
| C=S | 166.0 | 172.2 |
| H—H | 104.2 | 274.4 |
| N—N | 52.0 | 549.8 |
| N=N | 60.0 | 476.5 |
| N≡N | 226.0 | 126.6 |
| N—H (NH) | 85.0 | 336.4 |
| N—H (NH3) | 102.2 | 280.3 |
| N—O | 48.0 | 595.6 |
| N=O | 162.0 | 176.5 |
| O—O($O_2$) | 119.1 | 240.1 |
| —O—O— | 47.0 | 608.3 |
| O—H (water) | 117.5 | 243.3 |
| S—H | 83.0 | 344.5 |
| S—N | 115.2 | 248.6 |
| S—O | 119.0 | 240.3 |

Source: "The application of UV technology to pharmaceutical water treatment," Bakthisaran, S., European Journal of Parenteral Sciences, 3(4), pp. 97-102, 1998.

Turning to FIG. 1, a representation of a treatment chamber is depicted. Shown are a chamber 100 (also flux multiplying chamber), an ultraviolet lamp 102, an ultraviolet transmissive tube 104, a liquid 106, a light reflective material 108, and an optional transmissive tube (or lamp sleeve) 110. The chamber 100 contains an ultraviolet lamp 102 and a light transmissive tube 104. The ultraviolet lamp 102 may be enclosed by the optional transmissive tube 110. The chamber 100 may be coated or covered or lined with a light reflective material 108, as shown in FIG. 1. The ultraviolet lamp 102 may be located in a physically separate position, as shown in FIG. 1, from the ultraviolet transmissive tube 104. The light transmissive tube 104 runs through the chamber 100 where it is exposed to ultraviolet light provided by the ultraviolet lamp 102. The tube 104 may carry any type of liquid 106 or gas, including for example, water, air, experimental reagents, blood components (e.g. red blood cells, white blood cells, plasma) beverages for consumption, and the like. Therefore, as the liquid 106 passes through the ultraviolet transmissive tube 104, the liquid 106 is exposed to ultraviolet photons useful for sterilizing the liquid 106.

The chamber 100 of FIG. 1 has an input and output port (not shown) for an ultraviolet transmissive tube 104 to run through chamber 100. However, the input and output ports are fashioned as such to render the chamber 100 as substantially enclosed as possible. For example the input and/or output ports may utilize elbow, coiled, or other serpentine paths for gas and/or liquid flow to increase enclosure of the chamber. To further enhance enclosure, the flow path may be constricted to a smaller diameter and/or the reflector may be extended to a distance beyond the zone in which light is introduced. Additionally, certain features such as baffles may also be incorporated into the apparatus to optimize chamber concealment. In any case, any number and combination of the aforementioned techniques and devices may be used to increase chamber enclosure. As is further described hereinbelow, the apparatus reaches maximum efficiency when the chamber 100 approaches 100 percent enclosure and the reflective material approaches 100 percent reflectivity.

Although the chamber 100 depicted in FIG. 1 is coated with a reflective material 108, it should be understood that any type of reflective material or apparatus may be used. For example, the reflective material 108 which may be coated on the inside of the chamber 100 may be any of polyfetrafluoroethylene (PTFE), expanded polytetrafluoroethylene (ePTFE), or other similar plastics; or coated, anodized, or polished aluminum. In another embodiment, the reflective material 108 may be a reflector such as a diffuse or specular reflector. Any type of specular reflector, in any type of shape, may be used with the present embodiment. In any form, the reflective material 108 should have a high level of reflectivity. In one embodiment, the reflectivity level of the reflective material 108 is in the range of 80 percent to 100 percent, and more preferably, 90 percent to 100 percent.

Although the exact percent reflectivity may change depending on the particular needs of an apparatus, it should be understood that the higher the reflectivity, the higher the efficiency of the treatment chamber. For example, a fully enclosed chamber comprising a material with a 90 percent reflectivity in comparison to a fully enclosed chamber comprising a reflective material with a 99 percent reflectivity will have a lower dose on the target. Assuming that the exemplary target and walls are the only absorbers in the chamber, on average a photon will be reflected back and forth 10 times more in the 99 percent reflective chamber than the 90 percent reflective chamber before being absorbed by the reflective material. Thus, the photons are 10 times more likely to be absorbed by the target in a 99 percent reflective chamber than the 90 percent reflective chamber when the chamber is entirely enclosed. Therefore, the 99 percent reflective chamber delivers 10 times the ultraviolet light dose on the target as the 90 percent reflective chamber.

Similarly, a 99 percent enclosed chamber will deliver a higher ultraviolet light dose on a target than a 90 percent enclosed chamber. In a less enclosed chamber, photons are more likely to be reflected out of the chamber, thus reducing the likelihood of the photons being absorbed by the target. As such, the dosage of ultraviolet light treatment ultimately delivered to a target material is inversely related to absorbance where reflectivity of the apparatus components and enclosability of the chamber affects absorbance.

The ultraviolet lamp 102 may be of any type useful for providing ultraviolet radiation. For example, low pressure mercury lamps, medium pressure mercury lamps, excimer lamps, flashlamps with xenon and other fill mixtures, and microwave-driven lamps may be used with the present embodiment. The ultraviolet lamp provides at least one wavelength less than 400 nm to a target for the deactivation or killing of biological materials therein. The ultraviolet lamp 102 may be enclosed by the optional transmissive tube 110 which allows a technician to change out the lamp without opening the main chamber. Such a tube is optional and may be applied to the present embodiment for ease of operation; however, the present embodiment will function with out the lamp sleeve 110.

The ultraviolet transmissive tube 104 may be of any material that is substantially transmissive to ultraviolet light. To achieve maximum efficiency of the treatment chamber, it is preferable for the ultraviolet transmissive tube material to near 100 percent transmissivity as possible. In cases where 100 percent transmissivity is not possible, materials such as fused silica (Heraeus Heralux, GE Quartz Supersil), fluorine doped silica (Asahi Glass AQX), and sapphire (Saphikon EFG sapphire), being generally higher than 80 percent transmissive in the wavelengths below 300 nm, are useful.

Figure 2:
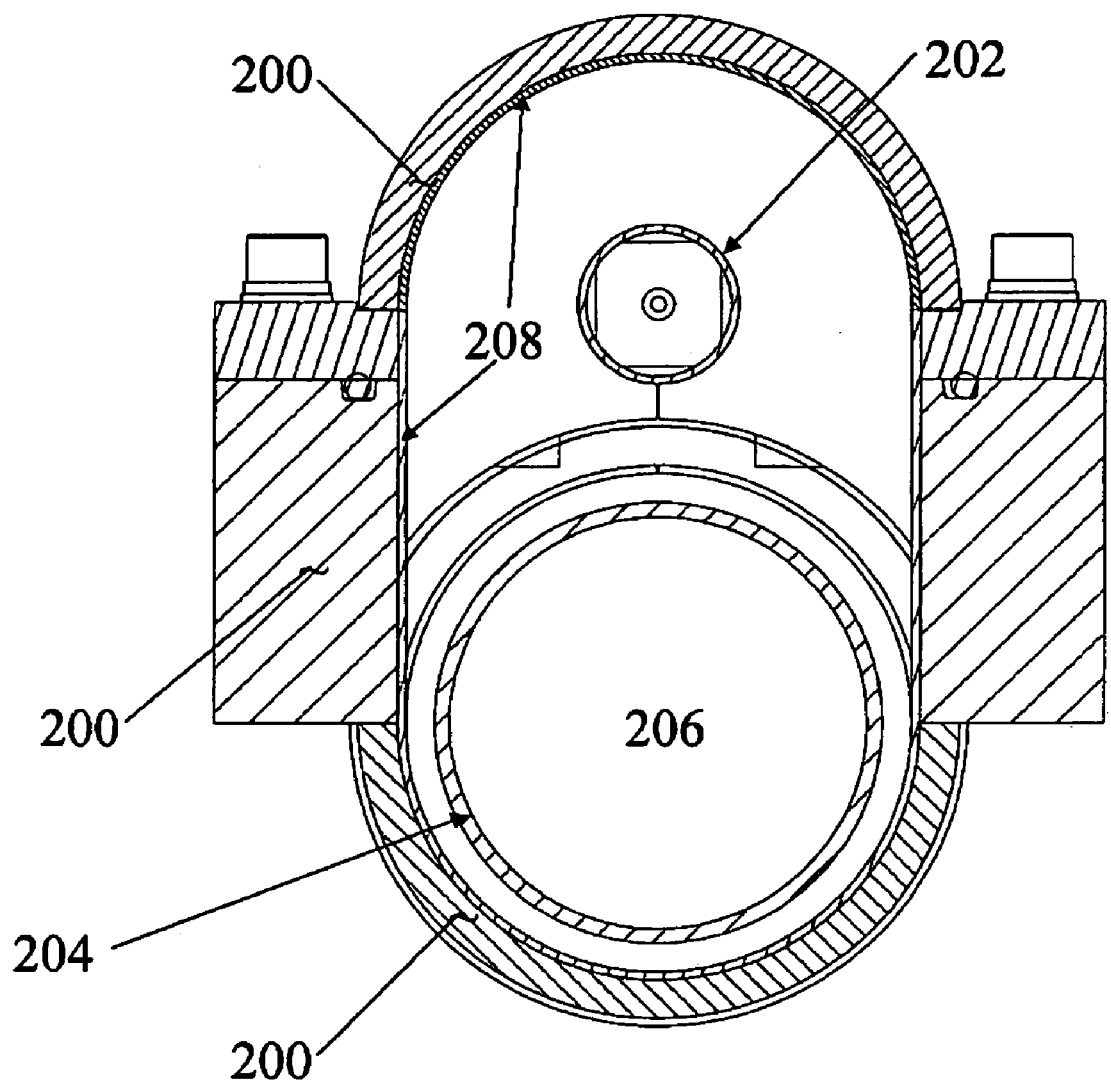
FIG. 2 is a drawing in an axial cross section of a treatment chamber of the present embodiment.

FIG. 2 is a drawing in an axial cross section of a treatment chamber. The treatment chamber consists of a chamber 200, an ultraviolet lamp 202, an ultraviolet transmissive tube 204, a liquid 206, and a light-reflective material 208. This chamber is functionally the same as that in FIG. 1. This chamber design maximizes the portion of the total chamber volume which is filled by the liquid 206. This ensures that the light spends the majority of its time between reflections within the liquid, which contains the target organisms or molecules. This increases the amount of light deposited in the. target over deigns in which the target volume is not a large fraction of the total treatment chamber volume.

Figure 3:
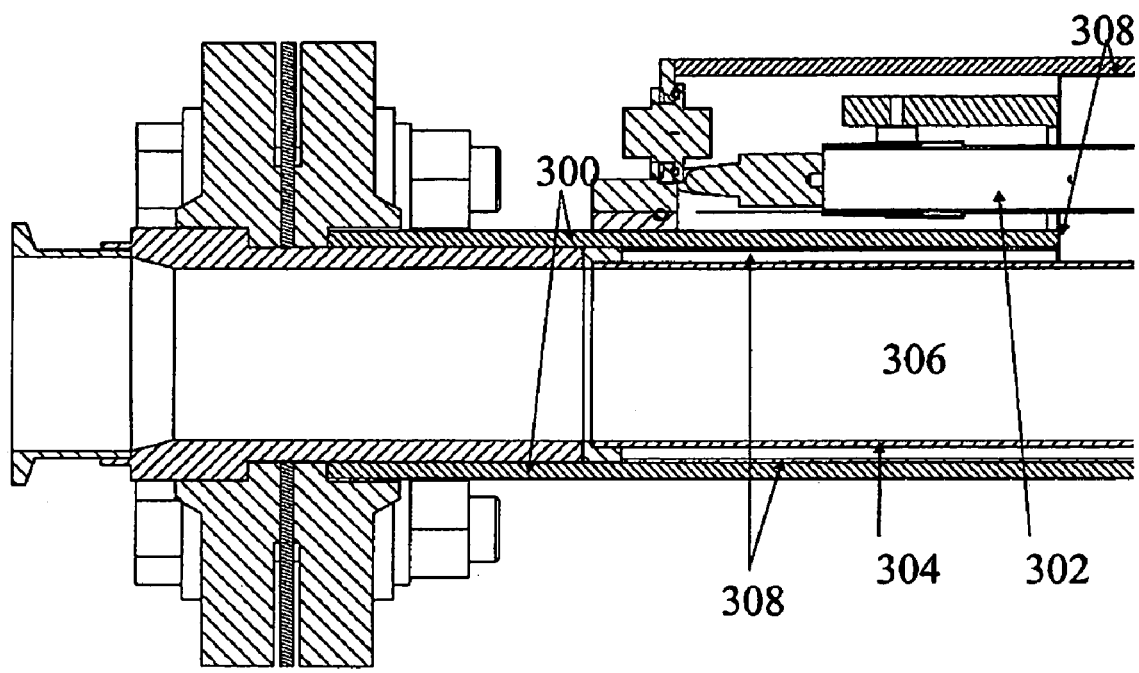
FIG. 3 is an illustration in longitudinal cross section of the present embodiment having an unobstructed flow path.

Turning now to FIG. 3, an illustration of the present embodiment having an unobstructed flow path depicts a portion of the longitudinal cross section of the same chamber. The components shown in this representation are a chamber 300, an ultraviolet lamp 302, an ultraviolet transmissive tube 304, a liquid 306, and a light-reflective material 308. The important feature shown in this drawing is that the chamber 300, the ultraviolet transmissive tube 304, and the reflector 308 are shaped such that the reflector 308 and the ultraviolet transmissive tube 304 extend along the longitudinal axis well beyond the ends of the active portion of the ultraviolet lamp 302. The extension of the reflector 308 and the ultraviolet transmissive tube 304 serves to re-direct the light which finds its way out of the volume of the chamber containing the active portion of the ultraviolet lamp 302 back into the liquid 306. It is possible to calculate the light loss in a structure like this compared to a simple hole in the wall. For a specular reflector, a simple ray tracing would suffice to quantify the loss. For a diffuse reflector, the problem is more complicated. The light from most diffuse reflectors is scattered in a Lambertian pattern. This is a benefit, as it tends to reflect more of the light back toward the opening from which it came than a specular reflector, but it increases the computation time by orders of magnitude. The best practice is to make the extension as long as is practical.

Figure 4:
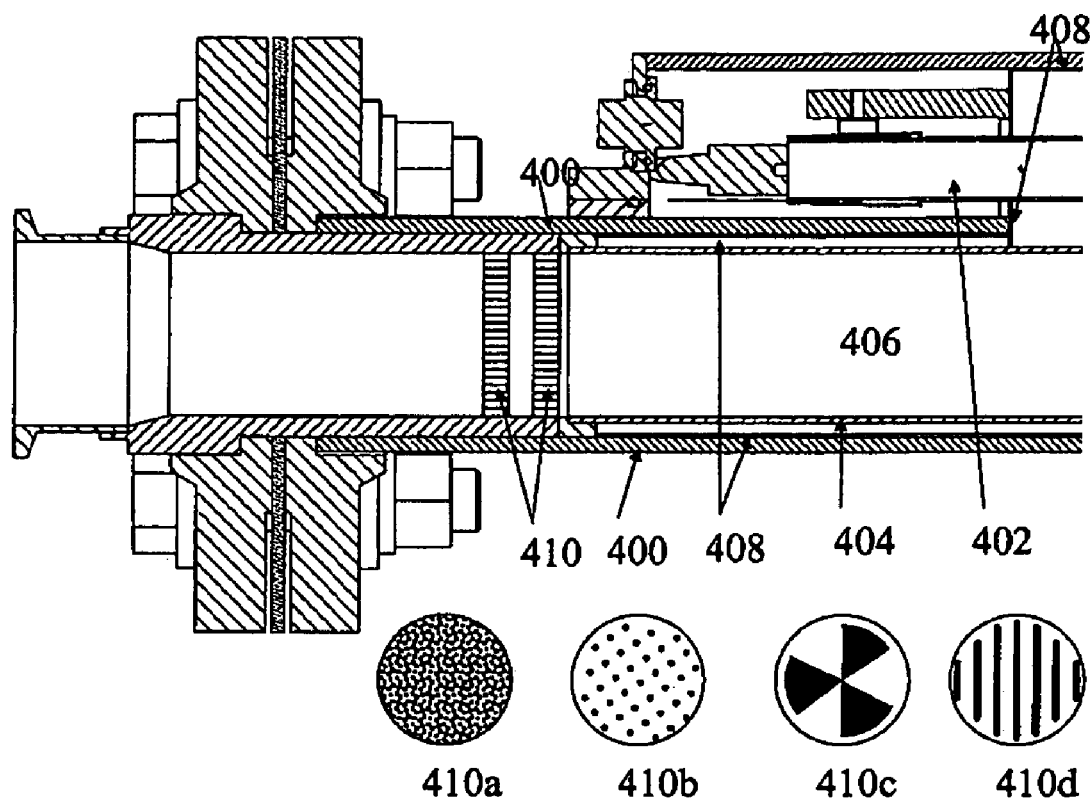
FIG. 4 is a drawing in longitudinal cross section of a portion of the present embodiment having light-reflecting baffles in the flow path.

FIG. 4 illustrates a cross section of a chamber similar to that of FIG. 3. Shown are a chamber 400, an ultraviolet lamp 402, an ultraviolet transmissive tube 404, a liquid 406, and a light-reflective material 408, and light reflecting baffles 410 installed at the end of the extensions to the ultraviolet transmissive tube 404 and light-reflective material 408. These baffles 410 reflect some or all of the light which impinge upon them back into the treatment chamber. They may be formed completely from or coated with the same material as the light-reflective material 408, or may have a different construction. They may be coated with fused silica or other ultraviolet transmissive material to separate the reflective material from the liquid 406. Four possible baffle types are shown as 410a, 410b, 410c, and 410d. 410a is a matrix with numerous small holes. 410b is a similar design, but with fewer, larger holes. 410c has three large openings. 410d has slots which are shown vertical but which could be mounted at any angle. Two baffles 410 are used to allow for orientation of the openings to minimize the amount of light escaping while allowing the liquid 406 to flow through freely. The porosity of these baffles is defined by the flow requirements of the liquid 406 and the desired level of containment of the light.

All references cited herein are incorporated by reference.

What is claimed is:

1. An apparatus for the treatment of a liquid, comprising:
   a chamber, wherein the chamber is at least 80 percent enclosed; and
   an ultraviolet lamp contained within the chamber; and
   an ultraviolet transmissive tube running through the chamber for the passage of liquid therethrough, wherein the liquid is substantially transmissive to ultraviolet light, and wherein substantially all light absorbing material contained within the chamber is contained within the ultraviolet transmissive tube; and
   a reflective material coating the chamber, wherein the material is at least 80 percent reflective.

2. The apparatus of claim 1, wherein the ultraviolet irradiance impinging on the liquid is in the range of about 0.01 W/cm$^2$ and 20 W/cm$^2$.

3. The apparatus of claim 1, wherein the reflective material is a reflector.

4. The apparatus of claim 3, wherein the reflector is any of the group consisting of a diffuse reflector and a specular reflector.

5. The apparatus of claim 3, wherein the reflector extends to a distance beyond the active portion of the ultraviolet lamp.

6. The apparatus of claim 4, wherein the reflector is comprised of any of the group consisting of PTFE, ePTFE, coated aluminum, anodized aluminum, and polished aluminum.

7. The apparatus of claim 1, wherein the reflective material is any of a mixture of a binder and a reflecting additive.

8. The apparatus of claim 7, wherein the reflecting additive is any of the group consisting of barium sulfate, magnesium fluoride, magnesium oxide, aluminum oxide, titanium oxide, holmium oxide, calcium oxide, lanthanum oxide, germanium oxide, tellurium oxide, europium oxide, erbium oxide, neodymium oxide, samarium oxide, ytterbium oxide, and zirconium oxide.

9. The apparatus of claim 1, further comprising baffles.

10. The apparatus of claim 1, further comprising an input and output port wherein the ultraviolet transmissive tube enters and exits the chamber.

11. The apparatus of claim 10, wherein said input port is configured in a serpentine path.

12. An apparatus for the treatment of a liquid, comprising:
    a chamber, wherein the chamber is at least 80 percent enclosed; and
    an ultraviolet lamp contained within the chamber; and
    an ultraviolet transmissive tube running through the chamber for the passage of liquid therethrough, wherein the liquid is substantially transmissive to ultraviolet light, and wherein substantially all light absorbing material contained within the chamber is contained within the ultraviolet transmissive tube; and
    a reflective material lining the inside of the chamber, wherein the material is at least 80 percent reflective.

13. The apparatus of claim 12, wherein the ultraviolet irradiance impinging on the liquid is in the range of about 0.01 W/cm$^2$ and 20 W/cm$^2$.

14. The apparatus of claim 12, wherein the reflective material is a reflector.

15. The apparatus of claim 14, wherein the reflector is any of the group consisting of a diffuse reflector and a specular reflector.

16. The apparatus of claim 14, wherein the reflector extends to a distance beyond the active portion of the ultraviolet lamp.

17. The apparatus of claim 15, wherein the reflector is comprised of any of the group consisting of PTFE, ePTFE, coated aluminum, anodized aluminum, and polished aluminum.

18. The apparatus of claim 12, wherein the reflective material is any of a mixture of a binder and a reflecting additive.

19. The apparatus of claim 18, wherein the reflecting additive is any of the group consisting of barium sulfate, magnesium fluoride, magnesium oxide, aluminum oxide, titanium oxide, holmium oxide, calcium oxide, lanthanum oxide, germanium oxide, tellurium oxide, europium oxide, erbium oxide, neodymium oxide, samarium oxide, ytterbium oxide, and zirconium oxide.

20. The apparatus of claim 12, further comprising baffles.

21. The apparatus of claim 12, further comprising an input and output port wherein the ultraviolet transmissive tube enters and exits the chamber.

22. The apparatus of claim 21, wherein said input port is configured in a serpentine path.

* * * * *